United States Patent
Kawahara et al.

(10) Patent No.: US 6,794,548 B2
(45) Date of Patent: Sep. 21, 2004

(54) METHOD OF PRODUCING 4,4'-BIPHENOL

(75) Inventors: Mikio Kawahara, Wakayama (JP); Toyokazu Kitaura, Wakayama (JP)

(73) Assignee: Honschu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 10/685,193

(22) Filed: Oct. 14, 2003

(65) Prior Publication Data

US 2004/0147790 A1 Jul. 29, 2004

(30) Foreign Application Priority Data

Jan. 23, 2003 (JP) ........................................ 2003-015260

(51) Int. Cl.[7] .............................................. C07C 39/12
(52) U.S. Cl. ...................................... 568/730; 568/805
(58) Field of Search ................................. 568/730, 805

(56) References Cited

U.S. PATENT DOCUMENTS

| | | | |
|---|---|---|---|
| 4,891,453 A | * | 1/1990 | Tanaka et al. ............... 568/730 |
| 5,099,076 A | | 3/1992 | Takahashi et al. |
| 5,324,868 A | * | 6/1994 | Inaba et al. .................. 568/805 |

FOREIGN PATENT DOCUMENTS

| | | |
|---|---|---|
| EP | 0 571 947 A1 | 12/1993 |
| JP | 2524594 | 5/1996 |
| JP | 3264976 | 12/2001 |

OTHER PUBLICATIONS

Database WPI Section Ch, Week 199032 Derwent Publications Ltd., London, GB; Class A41, AN 1990-242910 XP002274020.

Database Chemabs, Chemical Abstracts Service, Higo Atsushi et al: "Process for Production of 4,4'-biphenol with good color tone," XP002274019, Database accession No. 2002-594798.

Abstract of JP-63-301837 (1988).

Abstract of JP-05-331087 (1993).

* cited by examiner

Primary Examiner—Michael L. Shippen
(74) Attorney, Agent, or Firm—Knobbe, Martens, Olson & Bear LLP

(57) ABSTRACT

A method for producing 4,4'-biphenol, comprising the steps of:

preparing serially arranged reaction bathes for two or more steps; and carrying out a debutylation reaction of 3,3',5,5'-tetra-t-butyl-4,4'-biphenol sequentially in the presence of an acid catalyst in a reaction solvent by supplying at least one kind of phenols selected from the group consisting of phenol, monoalkylphenols, dialkylphenols, and trialkylphenols, in a proportion of at least 0.5 mole part relative to one mole part of 3,3',5,5'-tetra-t-butyl-4,4'-biphenol, to each reaction bath as a solvent for addition, wherein the number of carbon atoms of alkyl groups in alkylphenols consisting of the monoalkylphenols, dialkylphenols, and trialkylphenols, is each independently in the range of 1 to 4, and wherein a solvent for addition to a reaction bath for the latter step has a smaller average number of alkyl groups than a solvent for addition to a reaction bath for the former step.

10 Claims, 1 Drawing Sheet

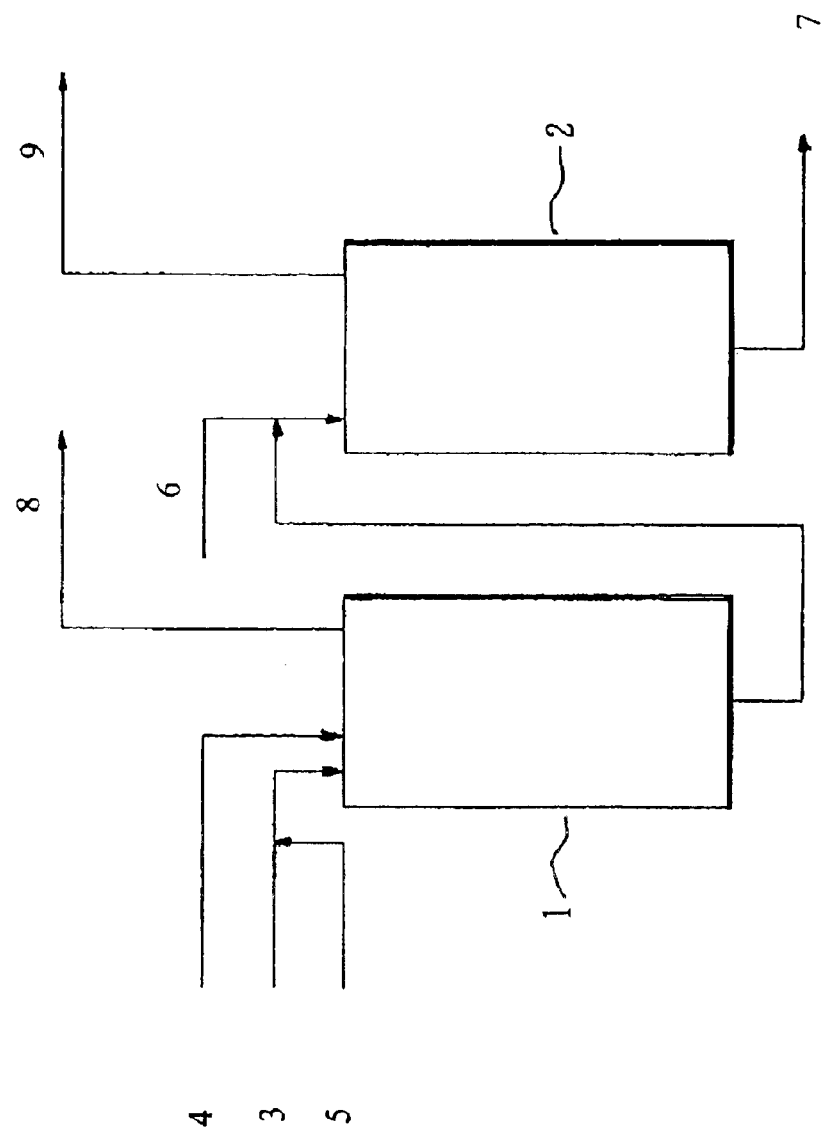

METHOD OF PRODUCING 4,4'-BIPHENOL

BACKGROUND OF THE INVENTION

1. Field of the Invention

The present invention relates to a method of producing 4,4'-biphenol, more specifically a method of producing 4,4'-biphenol with high efficiency and yield, in which 3,3', 5,5'-tetra-t-butyl-4,4'-biphenol is sequentially debutylated under relatively mild reaction conditions using reaction bathes arranged in series for two or more steps.

2. Description of the Related Art 4,4'-Biphenol (hereinafter referred to as BP) can be obtained by a debutylation reaction of 3,3',5,5'-tetra-t-butyl-4,4'-biphenol (hereinafter referred to as TBBP) and has been utilized as a raw material for liquid crystal polymers, super engineering plastics, and the like.

Conventionally, as a method for producing BP by a debutylation reaction of TBBP, a process by batch reaction is known (for example, see Japanese Patent Publication Laid-open No. 63-301837). A debutylation reaction of TBBP in the presence of an acid catalyst takes place sequentially and tri-t-butylbiphenol, di-t-butylbiphenol, mono-t-butylbiphenol and 4,4'-biphenol are produced one by one in this order; however, the rate of the debutylation reaction decreases with the decrease in the number of t-butyl groups. In particular, in order to debutylate mono-t-butylbiphenol with high yield, severe reaction conditions, such as a reaction temperature as high as 250° C. or higher and an extended reaction time, have to be used. Further, since a finally produced BP has an extremely low solubility in a reaction solvent, deposition of the product in the reaction solvent has to be controlled, for example, by using a large volume of the reaction solvent.

On the other hand, since generally a sequential process is economically advantageous over a batch process in industrial production of a large amount of chemicals, a sequential process for producing BP has been already suggested, in which TBBP is debutylated in a reaction solvent using serially arranged reaction bathes for multiple steps (for example, see Japanese Patent Publication Laid-open No. H05-331087). Thus, the abovementioned problem associated with sequential reactions has to be solved also in the sequential debutylation reaction of TBBP using serially arranged reaction for multiple steps. Accordingly, in the abovementioned method, a substituted aromatic hydrocarbon such as diethylbenzene is used as a reaction solvent and an acid catalyst is added in portions to each of the reaction bathes for multiple steps in an attempt to solve the abovementioned problem associated with sequential reactions.

However, according to the abovementioned method, as mentioned above, the catalyst has to be added in portions to each of the reaction bathes for multiple steps, which makes the reaction and operation complicated. Further, coloring impurity remains in the reaction product due to the catalyst used, which requires a purification process such as washing of the resulting reaction mixture with an alcohol mixture solvent after completing the reaction. Moreover, in the abovementioned method, when crude (unpurified) TBBP containing butylphenols, which is a reaction mixture of oxidation coupling reaction from 2,6-di-t-butylphenol, is used as a raw material, the reaction solvent becomes a mixture of butylphenols and a substituted aromatic hydrocarbon such as diethylbenzene, which also complicates fractionation and recovering of the solvent after the reaction.

SUMMARY OF THE INVENTION

An object of the present invention is to solve the abovementioned problem in the sequential debutylation reaction of TBBP using serially arranged reaction bathes for multiple steps and provide a method of sequentially producing 4,4'-biphenol under relatively mild reaction conditions with improved production yield and efficiency.

According to the present invention, there is provided a method of producing 4,4'-biphenol characterized in that a solvent for addition to a reaction bath for the latter step has a smaller average number of alkyl groups than a solvent for addition to a reaction bath for the former step in the method of producing 4,4'-biphenol in which using serially arranged reaction bathes for two or more steps, a debutylation reaction of 3,3',5,5'-tetra-t-butyl-4,4'-biphenol is sequentially carried out in the presence of an acid catalyst in a reaction solvent by supplying at least one kind of phenols selected from phenol, monoalkylphenols, dialkylphenols, and trialkylphenols (the number of carbon atoms of alkyl groups in alkylphenols, including these monoalkylphenols, dialkylphenols, and trialkylphenols, is each independently in the range of 1 to 4) in a proportion of at least 0.5 mole part to one mole part of material, i.e., 3,3',5,5'-tetra-t-butyl-4,4'-biphenol, to each reaction bath as the solvent for addition.

BRIEF DESCRIPTION OF THE DRAWINGS

Only one FIGURE is included, which is a schematic diagram showing one example of an apparatus for a sequential reaction to be preferably used in the present invention.

Explanation of symbols used is as follows:1: reaction bath; 2: reaction bath; 3: TBBP solution; 4: acid catalyst; 5: new solvent; 6; solvent; 7: reaction product; 8: isobutylene; 9: isobutylene.

DETAILED DESCRIPTION OF THE PREFERRED EMBODIMENT

In the present invention, "a reaction bath for the latter step" and "a reaction bath for the former step" are adjacent and accordingly the reaction bath for the latter step means a reaction bath immediately after the reaction bath for the former step. Further, "a solvent for addition" means a solvent to be added into each of the reaction bathes, which is at least one kind of solvent selected from phenol, monoalkylphenols, dialkylphenols, and trialkylphenols (the number of carbon atoms in alkyl groups in these monoalkylphenols, dialkylphenols, and trialkylphenols is each independently in the range of 1 to 4). However, when a material TBBP solution supplied into the first reaction bath contains a solvent which is included in the abovementioned solvent for addition, namely at least one kind of solvent selected from phenol, monoalkylphenols, dialkylphenols, and trialkylphenols (the number of carbon atoms in alkyl groups in these monoalkylphenols, dialkylphenols, and trialkylphenols is each independently in the range of 1 to 4), this solvent is to be included into a solvent for addition to the first reaction bath. A solvent for addition to reaction bathes for the second step and the subsequent steps means the abovementioned solvent to be added into the reaction bathes for the second step and the subsequent steps in addition to the solvent contained in a reaction mixture from the reaction bath for the former step. On the other hand, "a reaction solvent" implies all solvents contained in an individual reaction bath. Accordingly, the reaction solvent can be the same with or different from a solvent for addition in the first reaction bath; however, it is different from a solvent for addition in the second reaction bath and the subsequent reaction bathes.

Further, in the present invention, "the average number of alkyl groups" of a solvent for addition is an average expressed by the ratio of the total mole number of substituted alkyl groups to the total mole number of phenol and alkylphenols in the solvent for addition defined above. More specifically, the average number of alkyl groups is o for phenol, 1 for monobutylphenol, 2 for dibutylphenol, and 3 for tributylphenol. Accordingly, the average number of alkyl groups of a mixed solvent of 1 mole part of phenol and 1 mole part of monobutylphenol is 0.5 and the average number of alkyl groups of a mixed solvent of 1 mole part of monobutylphenol and 1 mole part of dibutylphenol is 1.5.

According to the present invention, a debutylation reaction of TBBP is sequentially carried out in the presence of an acid catalyst in a reaction solvent by supplying the abovementioned solvents for addition to each reaction bath using serially arranged reaction bathes for two or more steps. Here, the reaction bathes for two or more steps can be independent bathes arranged each other in series or the interior of a single reaction vessel is serially partitioned into a multiple reaction segments each of which forms the reaction bath.

According to the present invention, a material, TBBP, is supplied into the first reaction bath together with a catalyst. The material TBBP can be in any form as long as it can be continuously supplied into the first reaction bath at a constant rate; however, generally a material solution is prepared by dissolving the material in an appropriate organic solvent and continuously supplied into the first reaction bath at a constant rate. An organic solvent contained in such a material solution, in particular an organic solvent for use in preparing the material solution, is not particularly limited as long as it does not inhibit a debutylation reaction in the present invention. For example, phenol and alkylphenols, in particular butylphenols, are preferably used. However, an aromatic hydrocarbon is also used when appropriate.

Accordingly, in the present invention, examples of such a material solution include a solution in which purified TBBP is dissolved in butylphenol or a mixed solvent of butylphenol and phenol (hereinafter referred to as a "purified TBBP solution") and a reaction product which is produced by reacting phenol and isobutylene in the presence of aluminium phenoxide to produce 2,6-di-t-butylphenol and reacting the resulting reaction mixture as it is without isolating in the presence of an alkaline catalyst to produce TBBP containing the solvent (hereinafter referred to as a "crude TBBP solution.")

Preferable examples of the abovementioned butylphenols used as an organic solvent to obtain the abovementioned purified TBBP solution include mono-t-butylphenols such as p-t-butylphenol and o-t-butylphenol, di-t-butylphenols such as 2,6-di-t-butylphenol and 2,4-di-t-butylphenol, and tri-t-butylphenols such as 2,4,6-tri-t-butylphenol. These mono-, di- or tributylphenols can be used singly or as a mixture of two or more kinds. As mentioned above, these mono-, di- or tributylphenols to be used as organic solvent to obtain a purified TBBP solution are to be included in a solvent for addition to the reaction bath for the first step. However, according to the present invention, a solvent for addition can be supplied to the reaction bath for the first step in addition to these butylphenols used as an organic solvent to obtain a purified TBBP solution.

Thus, when a purified TBBP solution is used as a material solution, the amount of a solvent to be added for the first step is not particularly limited; however, generally, it ranges from 20 to 200% by weight, preferably 70 to 100% by weight.

On the other hand, the abovementioned crude TBBP solution contains solvents by itself as mentioned above. Namely, the crude TBBP solution contains, for example, about 1% by weight phenol, about 5% by weight o-t-butylphenol, about 15% by weight 2,4-di-t-butylphenol, and about 15% by weight 2,4,6-tri-t-butylphenol, and the like as solvents from the start along with the TBBP produced by the reaction. Thus, these phenol, mono-, di- or trialkylphenols contained from the start in the crude TBBP solution are also to be included in solvents for addition in the present invention. Accordingly, in the present invention, when a crude TBBP solution is used as a material TBBP solution, generally a solvent for addition may not be newly supplied; however, a solvent for addition may be newly supplied when appropriate.

In the present invention, as mentioned above, at least one kind of phenols selected from phenol, monoalkylphenols, dialkylphenols, and trialkylphenols (the number of carbon atoms in alkyl groups in these monoalkylphenols, dialkylphenols, and trialkylphenols is each independently in the range of 1 to 4) is used as a solvent for addition. Here according to the present invention, preferable specific examples of the abovementioned alkylphenols include t-butylphenols such as p-t-butylphenol, methylphenols such as cresols, dimethylphenols such as xylenol, mono- and diethylphenols, mono-and dipropylphenols, and mono-,di- and tributylphenols. However, according to the present invention, in particular, at least one kind of phenols selected from monobutylphenols, dibutylphenols and tributylphenols is preferably used as alkylphenols; among them, monobutylphenols, in particular mono-t-butylphenol, are preferably used.

In the present invention, when a debutylation reaction of TBBP is sequentially carried out in a reaction solvent by supplying solvents for addition to each reaction bath using serially arranged reaction bathes for two or more steps, solvents having a smaller average number of alkyl groups are used as the abovementioned solvents to be used as the reaction proceeds from the former step to the latter step in the reaction bathes for two or more steps. Namely, according to the present invention, the average number of alkyl groups of a solvent for addition to a reaction bath of the latter step is smaller than that of a solvent for addition to a reaction bath in the former step. Accordingly, when a reaction apparatus comprises reaction bathes for two steps, phenol, alkylphenols or a mixture thereof supplied as a solvent for addition into a reaction bath for the second step has a smaller average number of alkyl groups than that supplied into a reaction bath for the first step.

Accordingly, according to the present invention, a solvent to be added into a reaction bath for the latter step may vary depending on a solvent to be added into a reaction bath for the former step; in some cases a single solvent can be used, and in some cases various alkylphenols are mixed together with phenol to attain a desired average number of alkyl groups, when appropriate, and used as a solvent for addition. Thus, when various alkylphenols are mixed together with phenol to attain a desired average number of alkyl groups, when appropriate, a mixture of butylphenols and phenol is preferably used, and in particular a mixed solvent of p-t-butylphenol and phenol is preferably used.

More specifically, for example, when a reaction apparatus comprising serially arranged reaction bathes for two steps is used, the BP production rate is low in the first reaction bath. Therefore, a solvent for addition having a large average number of alkyl groups, for example, a solvent for addition having an average number of alkyl groups ranging from 0.8 to 3, preferably from 1 to 2, is used. On the other hand, as the BP production rate is high in the second reaction bath, a solvent for addition having an average number ranging from 0 to 0.5, preferably from 0 to 0.2, is supplied.

Accordingly, according to the present invention, in a preferred embodiment, a solvent for addition having a higher butylphenol content and a larger average number of alkyl groups is used in a reaction bath for the former step and a solvent for addition having a higher phenol content, and a smaller average number of alkyl groups is used in a reaction bath for the latter step.

Further according to the present invention, a solvent for addition in each reaction bath is used in an amount of at least 0.5 mole part per one mole part of material TBBP. That is because it is difficult to obtain BP of interest with high efficiency and yield when the solvent for addition in each reaction bath is used in an amount less than 0.5 mole part per one mole part of material TBBP. Accordingly, for example, when a reaction apparatus comprising reaction bathes for two steps is used, a solvent for addition is used preferably in an amount ranging from 0.5 to 5 mole parts per one mole part of material TBBP in the first reaction bath and in an amount ranging from 0.5 to 3 mole parts per one mole part of material TBBP. It is particularly preferable that a solvent for addition is used in an amount ranging from 2 to 3 mole parts per one mole part of material TBBP in the first reaction bath and together in an amount ranging from 1 to 2 mole parts per one mole part of material TBBP in the second reaction bath.

In the present invention, the total amount of solvents contained in all reaction bathes, namely the total amount of reaction solvents is not particularly limited; however it generally ranges from 1 to 10 mole parts, preferably 3 to 5 mole parts per one mole part of material TBBP from the viewpoint of transport of a reaction mixture obtained in each reaction bath and volumetric efficiency. As mentioned above, the reaction solvent mean all the solvents contained in an individual reaction bath. Accordingly, for example, when the reaction bathes comprise the first and the second reaction bathes, the reaction solvent means all solvents including a solvent for addition other than material TBBP in the first reaction bath and all solvents in a reaction mixture from the first reaction bath and a solvent for addition in the second reaction bath.

Next, according to the present invention, an acid catalyst is used as a catalyst for a debutylation reaction. Specific examples of this acid catalyst include organic sulfonic acid such as p-toluenesulfonic acid and benzenesulfonic acid, inorganic acids such as sulfuric acid, aluminium phenoxides, aluminium chloride, and Lewis acids such as ferric chloride. In particular, p-toluenesulfonic acid is preferably used.

The amount of such an acid catalyst to be used generally ranges from 0.05 to 5% by weight, preferably from 0.1 to 2% by weight, of purified TBBP, when the purified TBBP is used as a material. On the other hand, when the abovementioned crude TBBP is used as a material, an excess amount required for neutralization of an alkaline catalyst is added to the abovementioned amount since the crude TBBP usually contains the alkaline catalyst. In the present invention, an acid catalyst is continuously supplied into the reaction system; however, it can be supplied only to the first reaction bath or supplied to each reaction bath in portions. However, it is preferable to supply only into the first reaction bath because of easy reaction and operation.

The reaction temperature for a debutylation reaction of TBBP generally ranges from 150 to 250° C., preferably from 180 to 230° C., and most preferably from 200 to 220° C. In particular, according to the present invention, it is preferable to set the reaction temperature of a reaction bath higher as the reaction proceeds from the former step to the latter step, from the viewpoint of improving BP production. The reaction in each reaction bath can be carried out under atmospheric pressure or under pressure, for example, at 0.001 to 0.05 MPa (gauge pressure).

According to the present invention, the number of steps in the reaction apparatus using reaction bathes ranges preferably from 2 to 5 steps from the viewpoint of control and economic efficiency of the reaction. Further, retention time in reaction bathes for such multiple steps is 5 to 25 hours, preferably about 10 to 20 hours, as a total retention time for all steps. The retention time in a reaction bath for each step varies depending on selection of the reaction temperature and transformation rate in each reaction bath; however, it is generally preferable to set the retention time of the latter step shorter in terms of yield and quality.

Figure shows an example of sequential reaction apparatus to be preferably used in the present invention, which comprises a reaction bath 1 for the first step and a reaction bath 2 for the second step arranged in series. By using this reaction apparatus, as mentioned above, a material TBBP solution 3 and an acid catalyst 4, together with a new solvent 5 for addition, when appropriate, are sequentially supplied into the reaction bath 1 for the first step, and a reaction mixture obtained in the first reaction bath is consecutively transferred into the reaction bath 2 for the second step. Here, according to the present invention, a solvent 6 for addition having an average number of alkyl groups smaller than that of a solvent for addition supplied into the first reaction bath 1 is continuously supplied into the reaction bath 2 for the second step. In this way, a reaction product 7 containing BP of interest is continuously recovered from the second reaction bath 2. Isobutylene 8 and 9 released from the material in each reaction bath is discharged from the top of the reaction bath outside the reaction system.

EXAMPLES

The present invention will be explained by the following examples; however, these examples are not construed to limit the scope of the invention.

Example 1

A sequential apparatus shown in FIGURE was constructed by serially connecting two 1 L-glass autoclaves equipped with a stirrer, a thermometer and a pressure gauge. Into the first reaction bath were supplied a crude TBBP solution comprising 65% by weight TBBP, 15% by weight 2,6-di-t-butylphenol, 4% by weight o-t-butylphenol, and 14% by weight 2,4,6-tri-t-butylphenol at a rate of 60 g/hour, p-toluenesulfonic acid (catalyst) at a rate of 0.36 g/hour, and p-t-butylphenol at a rate of 21 g/hour, at a temperature of 210° C. and under pressure of 0.05 MPa (gauge pressure). Here, the solvents contained in the abovementioned crude TBBP solution, i.e., o-t-butylphenol, 2,6-di-t-butylphenol, and 2,4,6-tri-t-butylphenol, are solvents for addition into the first reaction bath, together with p-t-butylphenol and thus, the average number of alkyl groups in the solvents for addition in the first reaction bath was 1.5.

At the same time, phenol (its average number of alkyl groups is 0) was supplied at a rate of 15 g/hour as a solvent for addition into the second reaction bath at a tempeature of 220° C. and under pressure of 0.05 MPa (gauge pressure). Accordingly the average number of alkyl groups of the solvent for addition into the second reaction bath was 0.

Retention time was 8 hours each for the first reaction bath and the second reaction bath and thus the total retention time was 16 hours. After composition of the reaction mixture in each reaction bath was stabilized, the reaction mixtures released from the first reaction bath and the second reaction bath were analyzed by gas chromatography. The result showed that the BP production yield in the reaction mixture released from the first reaction bath was 65% by mole, and that the BP production yield in the reaction mixture released from the second reaction bath was 95% by mole. Further, the reaction mixtures were smoothly transferred from each reaction bath during reaction. Here, the BP production yield is defined as (mole number of BP produced/mole number of TBBP used)×100 (%) (hereinafter the same).

Example 2

Sequential reaction was carried out in the same manner as described in Example 1, except that phenol and p-t-butylphenol were supplied into the second reaction bath as solvents for addition at a rate of 13 g/hour and 2 g/hour, respectively. Accordingly, the average number of alkyl groups of the solvents for addition into the first reaction bath was the same as in Example 1, i.e., 1.5, and the average number of alkyl groups of the solvents for addition into the second reaction bath was 0.1.

After composition of the reaction mixture in each reaction bath was stabilized, the reaction mixtures released from the first reaction bath and the second reaction bath were analyzed by gas chromatography. The result showed that the BP production yield in the reaction mixture released from the first reaction bath was 65% by mole, and that the BP production yield in the reaction mixture released from the second reaction bath was 92% by mole. Further, the reaction mixtures were smoothly transferred from each reaction bath during reaction.

Example 3

Sequential reaction was carried out in the same manner as described in Example 1, except that the reaction temperature of the first reaction bath was set to 215° C. and p-t-butylphenol and phenol were supplied into the first reaction bath as solvents for addition at a rate of 18 g/hour and 3 g/hour, respectively. Accordingly, the average number of alkyl groups of the solvents for addition into the first reaction bath was 1.3, and the average number of alkyl groups of the solvent for addition into the second reaction bath was 0.

After composition of the reaction mixture in each reaction bath was stabilized, the reaction mixtures released from the first reaction bath and the second reaction bath were analyzed by gas chromatography. The result showed that the BP production yield in the reaction mixture released from the first reaction bath was 68% by mole, and that the BP production yield in the reaction mixture released from the second reaction bath was 94% by mole. Further, the reaction mixture was smoothly transferred between the reaction bathes during reaction.

Example 4

Sequential reaction was carried out in the same manner as described in Example 1, except that a 35% by weight p-t-butylphenol solution, i.e., purified TBBP solution, in place of the crude TBBP solution at a rate of 60 g/hour, p-toluenesulfonic acid at a rate of 0.06 g/hour in stead of 0.36 g/hour, and p-t-butylphenol at a rate of 21 g/hour instead of 14 g/hour were supplied into the first reaction bath. Accordingly, the average number of alkyl groups of the solvents for addition into the first reaction bath was 1, and the average number of alkyl groups of the solvents for addition into the second reaction bath was 0.

After composition of the reaction mixture in each reaction bath was stabilized, the reaction mixtures released from the first reaction bath and the second reaction bath were analyzed by gas chromatography. The result showed that the BP production yield in the reaction mixture released from the first reaction bath was 64% by mole, and that the BP production yield in the reaction mixture released from the second reaction bath was 94% by mole. Further, the reaction mixtures were smoothly transferred from each reaction bath during reaction.

Comparative Example 1

Sequential reaction was carried out in the same manner as described in Example 1, except that the reaction temperature of the first reaction bath was set to 205° C. and phenol was supplied as a solvent for addition into the first reaction bath at a rate of 21 g/hour and p-t-butylphenol was supplied as a solvent for addition into the second reaction bath at a rate of 15 g/hour. Accordingly, the average number of alkyl groups of the solvents for addition into the first reaction bath was 0.6, and the average number of alkyl groups of the solvents for addition into the second reaction bath was 1.0.

After composition of the reaction mixture in each reaction bath was stabilized, the reaction mixtures released from the first reaction bath and the second reaction bath were analyzed by gas chromatography. The result showed that the BP production yield in the reaction mixture released from the first reaction bath was 72% by mole, and that the BP production yield in the reaction mixture released from the second reaction bath was 83% by mole. Further, the reaction mixture was smoothly transferred from each reaction bath during reaction.

As mentioned above, according to the present invention, BP of interest can be obtained under relatively mild conditions attaining improved production yield and efficiency by making a solvent for addition into a reaction bath for the latter step to have a smaller average number of alkyl groups than a solvent for addition into a reaction bath of the former step in the method of producing BP in which using serially arranged reaction bathes for two or more steps, a debutylation reaction of TBBP is sequentially carried out in the presence of an acid catalyst in a reaction solvent by supplying at least one kind of solvent selected from phenol, monoalkylphenols, dialkylphenols, and trialkylphenols to each reaction bath as a solvent for addition.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method for producing 4,4'-biphenol, comprising the steps of:

preparing serially arranged reaction bathes for two or more steps; and carrying out a debutylation reaction of 3,3',5,5'-tetra-t-butyl-4,4'-biphenol sequentially in the presence of an acid catalyst in a reaction solvent by supplying at least one kind of phenols selected from the group consisting of phenol, monoalkylphenols, dialkylphenols, and trialkylphenols, in a proportion of at least 0.5 mole part relative to one mole part of 3,3',5,5'-tetra-t-butyl-4,4'-biphenol, to each reaction bath as a solvent for addition, wherein the number of carbon atoms of alkyl groups in alkylphenols consisting of said monoalkylphenols, said dialkylphenols, and said trialkylphenols, is each independently in the range of 1 to 4, and wherein a solvent for addition to a reaction bath for the latter step is at least one kind of said phenols having a smaller average number of alkyl groups than phenols used as a solvent for addition to a reaction bath for the former step.

2. The method according to claim 1, wherein said monoalkylphenols, dialkylphenols, and trialkylphenols are monobutylphenols, dibutylphenols and tributylphenols, respectively.

3. The method according to claim 1, wherein said at least one kind of phenols is phenol, p-t-butylphenol, or a mixture of phenol and p-t-butylphenol.

4. The method according to claim 1, wherein, when a reaction apparatus comprising serially arranged reaction bathes for two steps is used, the solvent for addition to a reaction bath for the former step is a solvent having an average number of alkyl groups ranging from 0.8 to 3, and the solvent for addition to a reaction bath for the latter step is a solvent having an average number ranging from 0 to 0.5.

5. The method according to claim 1, wherein a total amount of solvents contained in all reaction bathes is from 1 to 10 mole parts per one mole part of 3,3',5,5'-tetra-t-butyl-4,4'-biphenol.

6. The method according to claim 1, wherein said acid catalyst is an organic sulfonic acid.

7. The method according to claim 1, wherein a reaction temperature for the debutylation reaction is from 150 to 250° C.

8. The method according to claim 1, wherein the number of said reaction bathes is from 2 to 5 steps.

9. The method according to claim 1, wherein the reaction bathes for two or more steps are independent bathes arranged each other in series.

10. The method according to claim 1, wherein the reaction bathes for two or more steps are formed by serially partitioning the interior of a single reaction vessel into a multiple reaction segments.

* * * * *